US009920081B2

(12) United States Patent
Hansel et al.

(10) Patent No.: US 9,920,081 B2
(45) Date of Patent: *Mar. 20, 2018

(54) HALOGEN-FREE POLY(ALKYLENE PHOSPHATES)

(71) Applicant: LANXESS Deutschland GmbH, Leverkusen (DE)

(72) Inventors: Jan-Gerd Hansel, Bergisch Gladbach (DE); Heiko Tebbe, Dormagen (DE)

(73) Assignee: LANXESS Deutschland GmbH, Cologne (DE)

( * ) Notice: Subject to any disclaimer, the term of this patent is extended or adjusted under 35 U.S.C. 154(b) by 251 days.

This patent is subject to a terminal disclaimer.

(21) Appl. No.: 13/942,128

(22) Filed: Jul. 15, 2013

(65) Prior Publication Data
US 2014/0024734 A1 Jan. 23, 2014

(30) Foreign Application Priority Data

Jul. 20, 2012 (EP) ..................................... 12177287

(51) Int. Cl.
| C08K 5/521 | (2006.01) |
| C08L 75/08 | (2006.01) |
| C08L 75/06 | (2006.01) |
| C07F 9/141 | (2006.01) |
| C07F 9/09 | (2006.01) |
| C08G 18/48 | (2006.01) |
| C08G 18/42 | (2006.01) |
| C08G 101/00 | (2006.01) |
| C08K 5/00 | (2006.01) |

(52) U.S. Cl.
CPC .............. *C07F 9/141* (2013.01); *C07F 9/091* (2013.01); *C08G 18/42* (2013.01); *C08G 18/4825* (2013.01); *C08K 5/521* (2013.01); *C08L 75/06* (2013.01); *C08L 75/08* (2013.01); C08G 2101/0008 (2013.01); C08G 2101/0083 (2013.01); C08K 5/0066 (2013.01); C08K 2201/014 (2013.01)

(58) Field of Classification Search
None
See application file for complete search history.

(56) References Cited

U.S. PATENT DOCUMENTS

| 2,764,565 | A |   | 9/1956 | Hoppe et al. |
| 2,952,666 | A |   | 9/1960 | Coover et al. |
| 3,184,497 | A | * | 5/1965 | Brack ........................... 558/177 |
| 3,228,998 | A |   | 1/1966 | Fierce et al. |
| 3,767,732 | A |   | 10/1973 | Klose |
| 3,887,483 | A |   | 6/1975 | Morehouse |
| 3,891,727 | A |   | 6/1975 | Weil |
| 3,959,415 | A |   | 5/1976 | Shim et al. |
| 4,012,463 | A |   | 3/1977 | Walsh et al. |
| 4,056,480 | A | * | 11/1977 | Herber .......................... 252/78.5 |
| 4,248,930 | A |   | 2/1981 | Haas et al. |
| 4,263,408 | A |   | 4/1981 | Meyborg et al. |
| 4,382,042 | A |   | 5/1983 | Hardy et al. |
| 5,608,100 | A |   | 3/1997 | Sicken |
| 5,728,746 | A | * | 3/1998 | Sicken ........................... 521/169 |
| 5,944,650 | A | * | 8/1999 | Hu ............................. C11D 1/78 516/57 |
| 5,958,993 | A |   | 9/1999 | Blundell et al. |
| 5,985,965 | A |   | 11/1999 | Sicken et al. |
| 7,122,135 | B2 |   | 10/2006 | Williams et al. |
| 2007/0021516 | A1 | * | 1/2007 | Hansel ................... C08K 5/521 521/99 |
| 2009/0136440 | A1 | * | 5/2009 | Maas ..................... C08K 5/5317 424/78.08 |
| 2012/0184765 | A1 |   | 7/2012 | Hansel et al. |

FOREIGN PATENT DOCUMENTS

| CA | 2037809    | 9/1991 |
| CN | 101805620 A | 8/2010 |
| DE | 1694215 U  | 3/1955 |
| DE | 1720768 U  | 4/1956 |
| GB | 1162517    | 8/1969 |
| GB | 1211405 A  | 11/1970 |

OTHER PUBLICATIONS

European Search Report from co-pending Application EP12177287, dated Jan. 9, 2013, 2 pages.
European Search Report from related European Application EP15152591, dated Jul. 20, 2015, 4 pages.
Bliznyuk, N.K. et al., "Bis (.beta.-hydroxyethoxyphosphoryl) ethylene glycol", database accession No. 1976:16748, Chemical Abstracts Service, Columbus, Ohio, one page.
Vives, Jean Pierre et al, "Some cyclic phosphoric esters. I. Preparation and hydrolysis" database accession No. 1965:480110Chemical Abstracts Service, Columbus, Ohio, two pages.

* cited by examiner

Primary Examiner — Jeffrey Washville

(57) ABSTRACT

The present invention relates to halogen-free oligomer mixtures of poly(alkylene phosphates), production of these and use as flame retardants, and also to flame-retardant polyurethanes comprising halogen-free oligomer mixtures as flame retardants.

18 Claims, No Drawings

HALOGEN-FREE POLY(ALKYLENE PHOSPHATES)

The present invention relates to novel, halogen-free oligomer mixtures of poly(alkylene phosphates) and use of these for flame retardancy, in particular of polyurethanes, and also to polyurethane foams and polyurethanes thus modified, and processes for producing these.

Polyurethanes are used as plastics in many sectors, for example furniture, mattresses, transport, electrical, construction and technical insulation. In order to comply with the stringent flame retardancy requirements for materials inter alia for the field of interior fittings for automobiles, interior fittings for rail vehicles and interior fittings for aircraft, and also the flame retardancy requirements for buildings insulation, polyurethanes generally require modification with flame retardants. Many different flame retardants are known and commercially available for this purpose. However, use of these is often hindered by considerable problems relating to performance characteristics, or by toxicological concerns.

By way of example, use of solid flame retardants, e.g. melamine, ammonium polyphosphate and ammonium sulphate, encounters problems with metering technology which often necessitate modifications to the processing systems, i.e. complicated reengineering and adaptation.

Tris(chloroethyl) phosphate (molar mass 285 g/mol) and tris(chloroisopropyl) phosphate (molar mass 327 g/mol) are frequently used flame retardants, and are liquids that can easily be metered. However, a requirement increasingly placed upon open-cell flexible polyurethane foam systems for interior fittings in automobiles in recent times is that the gaseous emissions (volatile organic compounds, VOCs), and especially the condensable emissions (fogging) from said foams are to be minimized. The abovementioned liquids do not comply with the said requirements because they have relatively low molecular weights and therefore excessive volatility.

The term fogging means the undesired condensation of vaporized volatile constituents from the interior fittings of the motor vehicle onto panes of glass, in particular on the windscreen. This phenomenon can be assessed quantitatively in accordance with DIN 75 201.

Tris(2,3-dichloroisopropyl) phosphate is likewise liquid and with a molar mass of 431 g/mol its volatility is sufficiently low to permit achievement of acceptable fogging values. However, preference is often given to halogen-free flame retardant systems, for reasons of environmental toxicology, and also because of improved ancillary fire properties in relation to smoke density and smoke toxicity. Halogen-containing flame retardants are also considered problematic for reasons associated with performance characteristics: by way of example, when halogenated flame retardants are used severe corrosion phenomena are observed on the plant components used for flame lamination of polyurethane foams. This can be attributed to the hydrohalic acid emissions arising during the flame lamination of halogen-containing polyurethane foams.

Flame lamination is the term used for a process for the bonding of textiles and foams by using a flame for incipient melting of one side of a foam sheet and then immediately pressing a textile web onto this side.

The liquid halogen-free flame retardant systems known hitherto, e.g. triethyl phosphate or other alkyl or aryl phosphates, such as diphenyl cresyl phosphate, give only inadequate compliance with the abovementioned requirements for low levels of VOCs or low levels of fogging, or exhibit inadequate flame retardancy.

Oligomeric phosphoric esters provide solutions in the sense of low fogging contributions. These materials have been known for a long time, for example from U.S. Pat. No. 2,952,666 or U.S. Pat. No. 3,228,998. A disadvantage of the substances described in U.S. Pat. No. 2,952,666 is their inherently high content of acidic HO—P(=O)(OR)$_2$ groups. The substances described in U.S. Pat. No. 3,228,998 have two hydroxy groups per polymer chain. Acids, and also high content of hydroxy groups, are undesirable in the production of polyurethanes, since they disrupt the isocyanate reactions. By way of example, the quality of a polyurethane foam depends on balancing of the catalyst system with respect to the concurrent reactions of the polyisocyanates with the polyols and, where appropriate, with water. If another reactive component is introduced in the form of a hydroxylated flame retardant, production defects can occur, for example shrinkage or cracks in the foam. The catalyst system, often composed of a plurality of components, must then be balanced with respect to the reactivity of the flame retardant, while consideration is given to the stabilizers, blowing agents, cell regulators and any other constituents used. The said balancing requires time-consuming development work. It is moreover necessary to use an additional amount of polyisocyanate, and this is undesirable for economic reasons.

U.S. Pat. Nos. 3,767,732 and 4,382,042 by way of example moreover disclose a class of oligomeric phosphoric esters which have ethylene bridges and the structure of which can be described by the general formula

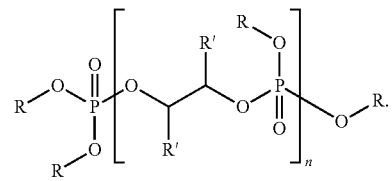

In this formula the substituents R are by way of example alkyl moieties, R' are H or alkyl moieties and the index n is an integer. These poly(ethylene phosphates) have achieved commercial significance because of their good effectiveness and low contributions to fogging: by way of example the product having the above formula where R=ethyl and R'=H is marketed with trade mark Fyrol® PNX by ICL-IP. WO 2002/079315 discloses flame retardant compositions which employ this active ingredient as flame retardant.

However, these known poly(ethylene phosphates) generally have the following disadvantages:

High viscosity. The high viscosity by way of example of Fyrol® PNX, 1241 mPas at 23° C. (see Comparative Examples), makes processing difficult.

Formation of ancillary components. Five-membered cyclic phosphates are formed during the production of the poly(ethylene phosphates) because they use ethylene bridges. These cyclic phosphates are present as ancillary components in the poly(ethylene phosphates), and lead to undesired ease of hydrolysis and acid formation. This problem has been known for a long time, and there have been numerous attempts to find a solution (cf. by way of example U.S. Pat. Nos. 3,891,727, 3,959,415, 3,959,414, 4,012,463 and EP-A 0 448 159). However, according to these proposed solutions, the avoidance or suppression of undesired five-membered cyclic phosphates always involves increased cost during the production of the poly(ethylene phosphates).

Restricted usage possibilities. Production of polyurethanes uses polyols from various structural classes. Particularly important classes are polyether polyols, i.e. hydroxylated polyethers, and polyester polyols, i.e. hydroxylated polyesters. It has been found that although the known poly(ethylene phosphates) have good processability in combination with polyether polyols, it is impossible to obtain useful foams in combination with polyester polyols (see Comparative Examples). This is a serious restriction in the scope of application of poly(ethylene phosphates), since machinery used for producing polyether foams with use of poly(ethylene phosphates) cannot also be used for producing polyester foams because of the risk of cross-contamination, even if the intention is to use other flame retardants. Producers wishing to produce not only polyether foams but also polyester foams must therefore not only double their logistical requirement to cope with two flame retardants hut must also maintain doubled machine capability.

WO 96/06885 also concerns the problem of fogging, and recommends straight-chain phosphoric esters having from 2 to 11 phosphoric ester groups as flame retardants for polyurethane foams. That document does not mention oligomer mixtures. The phosphoric esters preferably used in WO 96/06885 comprise aryl groups, such as phenyl groups. Aryl phosphates of this type are no longer accepted because of the unavoidable release of phenols hazardous to health under the conditions of use by way of example in the automobile industry.

It was therefore an object of the present invention to provide, for polyurethanes, halogen-free flame retardants which overcome the disadvantages mentioned of the prior art and which in particular can be processed with polyether polyols and also with polyester polyols, and minimize contributions to fogging.

The said object is achieved via flame retardants which comprise certain oligomer mixtures of halogen-free poly(alkylene phosphates).

The present invention therefore provides oligomer mixtures characterized in that they comprise at least three poly(alkylene phosphates) of the formula (I),

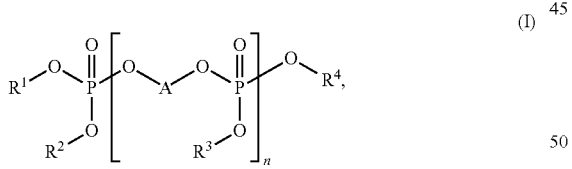

(I)

in which
$R^1$, $R^2$, $R^3$ and $R^4$ mutually independently respectively are a straight-chain or branched $C_1$-$C_8$-alkyl moiety or a straight-chain or branched $C_1$-$C_4$-alkoxyethyl moiety,
A is a straight-chain, branched and/or cyclic $C_4$-$C_{20}$-alkylene moiety, or
A is a moiety of the formula —$CH_2$—CH=CH—$CH_2$—, a moiety of the formula —$CH_2$—C≡C—$CH_2$—, a moiety of the formula —$CHR^5$—$CHR^6$—(O—$CHR^7$—$CHR^8$)$_a$—, a moiety of the formula —$CHR^5$—$CHR^6$—S(O)$_b$—$CHR^7$—$CHR^8$— or a moiety of the formula —($CHR^5$—$CHR^6$—O)$_c$—$R^9$—(O—$CHR^7$—$CHR^8$)$_d$—,
in which
a is an integer from 1 to 5,
b is an integer from 0 to 2,
c and d are mutually independently an integer from 1 to 5,
$R^5$, $R^6$, $R^7$ and $R^8$ are mutually independently H or methyl,
$R^9$ is a moiety of the formula—$CH_2$—CH=CH—$CH_2$—, a moiety of the formula —$CH_2$—C≡C—$CH_2$—, a 1,2-phenylene moiety, a 1,3-phenylene moiety, a 1,4-phenylene moiety, or a moiety of the formula (II)

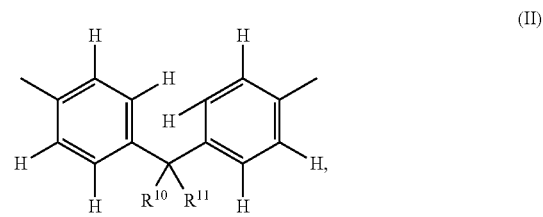

(II)

a moiety of the formula (III)

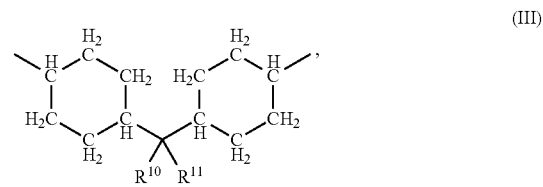

(III)

a moiety of the formula (IV)

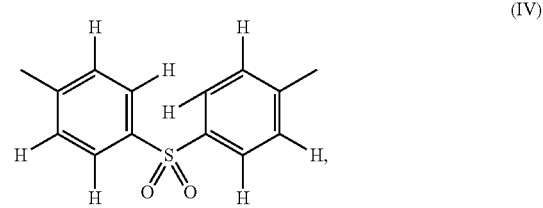

(IV)

or a moiety of the formula —C(=O)—$R^{12}$—C(=O)—,
where
$R^{10}$ and $R^{11}$ are mutually independently respectively H or $C_1$-$C_4$-alkyl or $R^{10}$ and $R^{11}$ together are an optionally alkyl-substituted ring having from 4 to 8 carbon atoms,
$R^{12}$ is a straight-chain, branched and/or cyclic $C_2$-$C_8$-alkylene moiety, a 1,2-phenylene moiety, a 1,3-phenylene moiety, or a 1,4-phenylene moiety, and
n is an integer from 0 to 100,
with the proviso that the at least three poly(alkylene phosphates) of the formula (I) differ from one another at least in the number n of the repeating units, and
the average number of the repeating units $\bar{n}$ of the at least three poly(alkylene phosphates) of the formula (I) is greater than 1.10 and smaller than 2.00.

It is preferable that $R^1$, $R^2$, $R^3$ and $R^4$ are identical and are either ethyl, n-propyl, isopropyl, n-butyl, isobutyl or n-butoxyethyl. It is preferable that A is a straight-chain $C_4$-$C_6$-alkylene moiety.

It is further preferable that A is a moiety of the formula (II), in which $R^{10}$ and $R^{11}$ are identical and are methyl, or a moiety of the formulae (V), (VI) or (VII),

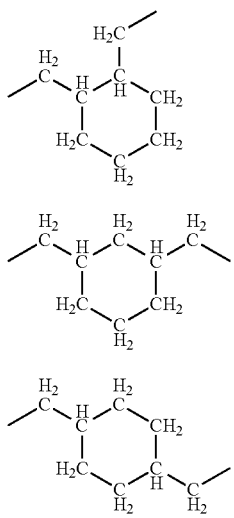

(V)

(VI)

(VII)

It is equally preferable that A is a moiety of the formula —CHR$^5$—CHR$^6$—(O—CHR$^7$—CHR$^8$)$_a$—, in which a is a number from 1 to 2 and R$^5$, R$^6$, R$^7$ and R$^8$ are identical and are H, or a moiety of the formula —(CHR$^5$—CHR$^6$—O)$_c$—R$^9$—(O—CHR$^7$—CHR$^8$)$_d$—, in which c and d are mutually independently an integer from 1 to 2, and R$^9$ is a moiety of the formula (II), where R$^{10}$ and R$^{11}$ are identical and are methyl.

Preference is given to oligomer mixtures comprising at least three poly(alkylene phosphates) of the formula (I), in which R$^1$, R$^2$, R$^3$ and R$^4$ are mutually independently respectively a straight-chain or branched C$_1$-C$_4$-alkyl moiety or a C$_1$- or C$_2$-alkoxyethyl moiety, A is a straight-chain or branched C$_4$-C$_{10}$-alkylene moiety, or A is a moiety of the formula —CH$_2$—CH=CH—CH$_2$—, a moiety of the formula —CH$_2$—C≡C—CH$_2$—, a moiety of the formula —CHR$^5$—CHR$^6$—(O—CHR$^7$—CHR$^8$)$_a$—, a moiety of the formula —CHR$^5$—CHR$^6$—S(O)$_b$—CHR$^7$—CHR$^8$— or a moiety of the formula —(CHR$^5$—CHR$^6$—O)$_c$—R$^9$—(O—CHR$^7$—CHR$^8$)$_d$—, in which a is an integer from 1 to 5,
b is an integer from 0 to 2,
c and d are mutually independently an integer from 1 to 5,
R$^5$, R$^6$, R$^7$ and R$^8$ are mutually independently H or methyl,
R$^9$ is a moiety of the formula —CH$_2$—CH=CH—CH$_2$—, a moiety of the formula —CH$_2$—C≡C—CH$_2$—, a 1,2-phenylene moiety, a 1,3-phenylene moiety, a 1,4-phenylene moiety, or a moiety of the formula (II)

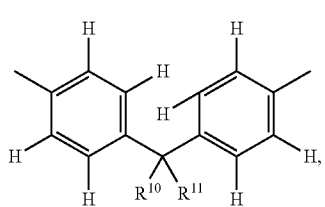

(II)

a moiety of the formula (III)

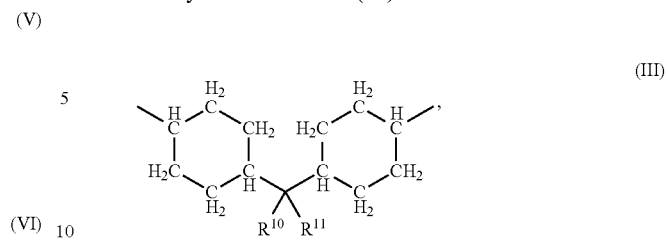

(III)

a moiety of the formula (IV)

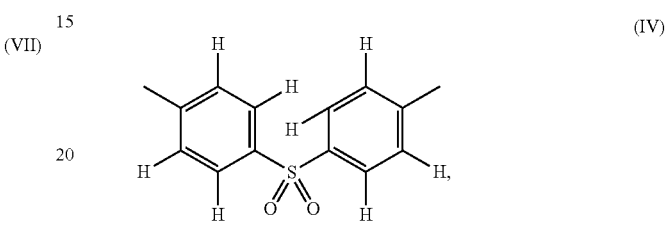

(IV)

or a moiety of the formula —C(=O)—R$^{12}$—C(=O)—, where

R$^{10}$ and R$^{11}$ are mutually independently respectively H or C$_1$- or C$_2$-alkyl,
R$^{12}$ is a straight-chain or branched C$_2$-C$_6$-alkylene moiety, a 1,2-phenylene moiety, a 1,3-phenylene moiety, or a 1,4-phenylene moiety, and
n is an integer from 0 to 100.

Very particular preference is given to oligomer mixtures comprising at least three poly(alkylene phosphates) of the formula (I)
in which
R$^1$, R$^2$, R$^3$ and R$^4$ are mutually independently respectively a straight-chain or branched C$_1$-C$_4$-alkyl moiety or an n-butoxyethyl moiety,
A is a straight-chain C$_4$-C$_6$-alkylene moiety, or
A is a moiety of the formula —CH$_2$—CH=CH—CH$_2$—, a moiety of the formula —CH$_2$—C≡C—CH$_2$—, a moiety of the formula —CHR$^5$—CHR$^6$—(O—CHR$^7$—CHR$^8$)$_a$—, a moiety of the formula —CHR$^5$—CHR$^6$—S(O)$_b$—CHR$^7$—CHR$^8$— or a moiety of the formula —(CHR$^5$—CHR$^6$—O)$_c$—R$^9$—(O—CHR$^7$—CHR$^8$)$_d$—,
in which
a is an integer from 1 to 5,
b is an integer from 0 to 2,
c and d are mutually independently an integer from 1 to 5,
R$^5$, R$^6$, R$^7$ and R$^8$ are mutually independently H or methyl,
R$^9$ is a moiety of the formula —CH$_2$—CH=CH—CH$_2$—, a moiety of the formula —CH$_2$—C≡C—CH$_2$—, a 1,2-phenylene moiety, a 1,3-phenylene moiety, a 1,4-phenylene moiety, or a moiety of the formula (II)

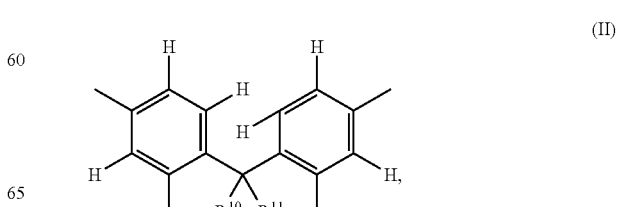

(II)

a moiety of the formula (III)

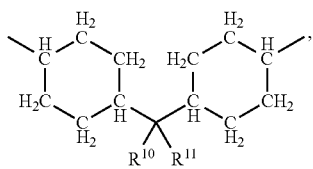
(III)

a moiety of the formula (IV)

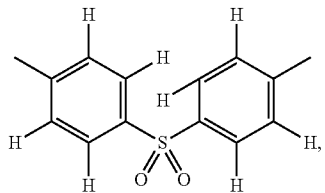
(IV)

or a moiety of the formula —C(=O)—R$^{12}$—C(=O)—, where

R$^{10}$ and R$^{11}$ are mutually independently respectively H or C$_1$ or C$_2$-alkyl, R$^{12}$ is a straight-chain or branched C$_2$-C$_6$-alkylene moiety, a 1,2-phenylene moiety, a 1,3-phenylene moiety, or a 1,4-phenylene moiety, and n is an integer from 0 to 100.

In particular, preference is given to oligomer mixtures comprising at least three poly(alkylene phosphates) of the formula (I)
in which
R$^1$, R$^2$, R$^3$ and R$^4$ are identical and are ethyl, n-propyl, isopropyl, n-butyl, isobutyl or n-butoxyethyl,
A is a straight-chain C$_4$-C$_6$-alkylene moiety, or
A is a moiety of the formulae

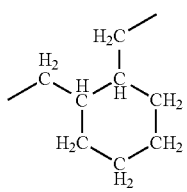
(V)

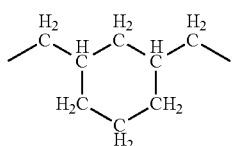
(VI)

or

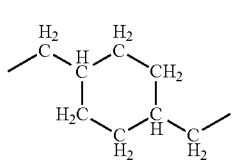
(VII)

or
A is a moiety —CHR$^5$—CHR$^6$—(O—CHR$^7$—CHR$^8$)$_a$—, in which a is an integer from 1 to 2 and R$^5$, R$^6$, R$^7$ and R$^8$ are identical and are H, or a moiety —(CHR$^5$—CHR$^6$—O)$_c$—R$^9$—(O—CHR$^7$—CHR$^8$)$_d$—, in which c and d are mutually independently an integer from 1 to 2, R$^5$, R$^6$, R$^7$ and R$^8$ are identical and are H, R$^9$ is a moiety of the formula (II), where R$^{10}$ and R$^{11}$ are identical and are methyl,
and
n is an integer from 0 to 20.

It is preferable that the oligomer mixtures according to the invention and the poly(alkylene phosphates) present therein are halogen-free. For the purposes of the present invention, the term "halogen-free" means that the poly(alkylene phosphates) of the formula (I) do not comprise the elements fluorine, chlorine, bromine and/or iodine and that the oligomer mixtures according to the invention do not comprise any other substances in an amount which is the cause of content greater than 5000 ppm, based on the oligomer mixture, of one or more of the elements fluorine, chlorine, bromine and iodine.

The oligomer mixtures according to the invention comprise at least three, preferably more than three, different poly(alkylene phosphates) of the general formula (I) which differ from one another at least in the number n of the repeating units and thus in their molar mass. The person skilled in the art describes oligomer mixtures of this type by using suitable average values, for example the number-average molar mass M$_n$ and the average number of repeating units $\bar{n}$ of the molecules of the formula (I) present in the oligomer mixture.

According to the invention, the number-average molar mass M$_n$ of the poly(alkylene phosphates) present in the oligomer mixtures is determined via gel permeation chromatography with tetrahydrofuran as eluent against polystyrene standards. This method is known to the person skilled in the art, for example from DIN 55672-1:2007-08. From M$_n$ it is easily possible by taking into account the stoichiometry of the formula (I) to calculate the average number of the repeating units $\bar{n}$ of the poly(alkylene phosphates) present in the oligomer mixture (see Examples).

An essential feature of the present invention is the surprising finding that the only oligomer mixtures of poly (alkylene phosphates) of the formula (I) that exhibit the desired combination of properties are those whose average number of the repeating units $\bar{n}$ if of the poly(alkylene phosphates) of the formula (I) present in the oligomer mixture is greater than 1.10 and smaller than 2.00. The oligomer mixtures according to the invention are characterized by good flame-retardant effectiveness, low fogging level, low viscosity and good processability not only with polyether polyols but also with polyester polyols.

The average number of the repeating units $\bar{n}$ in the poly(alkylene phosphates) of the formula (I) present in the oligomer mixtures according to the invention is preferably greater than 1.20 and smaller than 1.90.

The oligomer mixtures according to the invention can in principle be produced via methods known to the person skilled in the art for producing alkyl phosphates. By way of example, the oligomer mixtures according to the invention can be produced via the reaction of alkyl dichlorophosphates of the formula MO-POCl$_2$, in which M is a moiety R$^1$, R$^2$, R$^3$ or R$^4$ and R$^1$, R$^2$, R$^3$ and R$^4$ comply with the general and preferred definitions stated above, with dihydroxy compounds of the formula HO-A-OH, in which A complies with the general and preferred definitions stated above, and with one or more monohydroxy compounds M-OH, in which M is defined as above, or via reaction of dihydroxy compounds of the formula HO-A-OH, in which A complies with the general and preferred definitions stated above, with phosphorus oxychloride $POCl_3$ and with one or more monohydroxy compounds M-OH, in which M is a moiety $R^1$, $R^2$, $R^3$ or $R^4$, and $R^1$, $R^2$, $R^3$ and $R^4$ comply with the general and preferred definitions stated above, or via reaction of one or more trialkyl phosphates $(MO)_3PO$, in which M is defined as above, with phosphorus pentoxide $P_2O_5$ and with a cyclic ether.

According to the invention, preference is given to production via reaction of dihydroxy compounds HO-A-OH, in which A complies with the general and preferred definitions stated above, with phosphorus oxychloride $POCl_3$ and with one or more monohydroxy compounds M-OH, in which M is a moiety $R^1$, $R^2$, $R^3$ or $R^4$, and $R^1$, $R^2$, $R^3$ and $R^4$ comply with the general and preferred definitions stated above.

The present invention further provides a process for producing the oligomer mixtures according to the invention, characterized in that, in a first stage, a dihydroxy compound of the formula HO-A-OH, in which A complies with the general and preferred definitions stated above, is reacted with phosphorus oxychloride $POCl_3$, where the amount of $POCl_3$ used per mole of dihydroxy compound of the formula HO-A-OH is more than 1.0 mol and less than 2.0 mol, and the resulting mixture of oligomeric chlorophosphates of the formula (VIII)

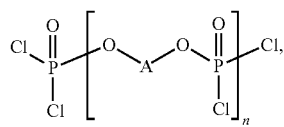

(VIII)

in which n is an integer from 0 to 100, is further reacted in a second stage with at least one monohydroxy compound of the formula

M-OH (IX), in which M is $R^1$, $R^2$, $R^3$ or $R^4$, and
$R^1$, $R^2$, $R^3$ and $R^4$ comply with the general and preferred definitions stated above,
to give the oligomer mixtures according to the invention.

The monohydroxy compounds of the formula (IX) used for producing the oligomer mixtures according to the invention can be identical or different.

The amount of $POCl_3$ used for producing the oligomer mixtures according to the invention is preferably from 1.45 to 1.8 mol per mole of dihydroxy compound of the formula HO-A-OH.

The types of experimental series with which the person skilled in the art is familiar can easily be used to determine the most advantageous molar ratio, within the range stated above, of dihydroxy compounds HO-A-OH to phosphorus oxychloride $POCl_3$ for producing the oligomer mixture according to the invention with an average number of repeating units $\bar{n}$ greater than 1.10 and smaller than 2.00.

The process according to the invention can be carried out within a wide temperature range. The process according to the invention is generally carried out in the temperature range from 0 to 100° C. It is preferable to operate at a temperature from 5 to 40° C. in the first stage and generally to operate at a temperature of from 5 to 30° C. in the second stage.

The process according to the invention can be carried out within a wide pressure range. It is preferable to carry out the first stage at a pressure of from 10 to 1000 mbar and to carry out the second stage at atmospheric pressure.

It is preferable that the oligomer mixtures according to the invention involve compounds that are liquid at processing temperature. The expression processing temperature here means the temperature at which the polyurethane raw materials are introduced into the metering and mixing assemblies of the production plants. Temperatures selected here are generally from 20 to 80° C., depending on the viscosities of the components and the design of the metering assemblies.

The viscosity of the oligomer mixtures according to the invention at 23° C. is preferably less than 1000 mPas. It is particularly preferable that the viscosity at 23° C. is less than 500 mPas.

It is preferable that the oligomer mixtures according to the invention have low volatility.

It is preferable that the oligomer mixtures according to the invention are inert with respect to the other starting materials used for producing the polyurethanes, in particular with respect to isocyanates.

The oligomer mixtures according to the invention are suitable for use as flame retardants and for producing flame retardant preparations.

The present invention provides the use of the oligomer mixtures according to the invention as flame retardants.

The oligomer mixtures according to the invention can generally be used in any of the applications known to the person skilled in the art for flame retardants. It is preferable that the oligomer mixtures according to the invention are used as flame retardants for synthetic polymers, such as polyolefins, polycarbonates, styrene-based (co)polymers, polyamides, polyesters and epoxy resins, for plant-based materials, such as wood, wood-plastic composites, paper and paper board, and for materials of animal origin, such as leather.

The present invention also provides flame retardant preparations comprising at least one oligomer mixture according to the invention, at least one other flame retardant B) and optionally one or more auxiliaries C) selected from the group consisting of solvents, antioxidants, stabilizers and colourants.

It is preferable that the flame retardant preparations according to the invention comprise, as other flame retardant B), at least one flame retardant selected from the group consisting of triethyl phosphate, triphenyl phosphate, diphenyl cresyl phosphate, tricresyl phosphate, isopropylated or butylated aryl phosphates, bisphenol A bis(diphenyl phosphate), resorcinol bis(diphenyl phosphate), neopentyl glycol bis(diphenyl phosphate), tris(chloroisopropyl) phosphate, tris(dichloropropyl) phosphate, dimethyl methanephosphonate, diethyl ethanephosphonate, dimethyl propanephosphonate, diethyl phosphinic acid derivatives and diethyl phosphinic acid salts, other oligomeric phosphates or phosphonates, hydroxylated phosphorus compounds, 5,5-dimethyl-1,3,2-dioxaphosphorinane 2-oxide derivatives, 9,10-dihydro-9-oxa-10-phosphaphenanthrene 10-oxide (DOPO) and its derivatives, ammonium phosphate, ammonium polyphosphate, melamine phosphate, melamine polyphosphate, melamine, melamine cyanurate, alkyl ester of a tetrabromobenzoic acid, bromine-containing diols produced from tetrabromophthalic anhydride, bromine-containing polyols, bromine-containing diphenyl ethers, aluminium hydroxide, boehmite, magnesium hydroxide, expandable graphite and clay minerals.

Example of auxiliaries C) that can be used are solvents, e.g. water or alkyl esters of aliphatic or aromatic di- or tricarboxylic acids, antioxidants and stabilizers, e.g. sterically hindered trialkylphenols, alkyl esters of 3-(3,5-di-tert-butyl-4-hydroxyphenyl)propionic acid, benzofuran-2-ones, secondary aromatic amines, phosphites, phenothiazines or tocopherols, and colourants, e.g. iron oxide pigments or carbon blacks.

The present invention further provides flame-retardant polyurethanes comprising at least one oligomer mixture according to the invention.

The flame-retardant polyurethanes according to the invention can be produced by reacting organic polyisocyanates with compounds having at least two hydrogen atoms reactive towards isocyanates, optionally with conventional blowing agents, stabilizers, activators and/or other conventional auxiliaries and additives and in the presence of at least one oligomer mixture according to the invention.

The amount used of the oligomer mixtures according to the invention is from 0.5 to 30 parts by weight, preferably from 3 to 25 parts by weight, based on 100 parts by weight of polyol component.

The polyurethanes involve isocyanate-based polymers which have predominantly urethane groups and/or isocyanurate groups and/or allophanate groups and/or uretdione groups and/or urea groups and/or carbodiimide groups. The production of isocyanate-based polymers is known per se and is described by way of example in German Offenlegungsschrift 16 94 142, German Offenlegungsschrift 16 94 215 and German Offenlegungsschrift 17 20 768, and also in Kunststoff-Handbuch Band VII, Polyurethane [Plastics handbook Volume VII, Polyurethanes], edited by G. Oertel, Carl-Hanser-Verlag Munich, Vienna 1993.

The polyurethanes according to the invention involve thermoset polyurethanes, polyurethane foams, polyurethane elastomers, thermoplastic polyurethanes, polyurethane coatings and polyurethane lacquers, polyurethane adhesives and polyurethane binders or polyurethane fibres.

In one preferred embodiment of the invention, the polyurethanes according to the invention involve polyurethane foams.

Polyurethane foams are broadly divided into flexible and rigid foams. Although flexible and rigid foams can in principle have approximately the same envelope density and constitution, flexible polyurethane foams have only a low degree of crosslinking and have only a low resistance to deformation under pressure. In contrast to this, the structure of rigid polyurethane foams is composed of highly crosslinked units, and rigid polyurethane foam has very high resistance to deformation under pressure. The typical rigid polyurethane foam is of closed-cell type and has only a low coefficient of thermal conductivity. In the production of polyurethanes, which proceeds by way of the reaction of polyols with isocyanates, the subsequent structure of the foam and its properties are influenced primarily by way of the structure and molar mass of the polyol and also by way of the reactivity and number (functionality) of the hydroxy groups present in the polyol. Further details concerning rigid and flexible foams and the starting materials that can be used for their production, and also concerning processes for their production, are found in Norbert Adam, Geza Avar, Herbert Blankenheim, Wolfgang Friederichs, Manfred Giersig, Eckehard Weigand, Michael Halfmann, Friedrich-Wilhelm Wittbecker, Donald-Richard Larimer, Udo Maier, Sven Meyer-Ahrens, Karl-Ludwig Noble and Hans-Georg Wussow: "Polyurethanes", Ullmann's Encyclopedia of Industrial Chemistry Release 2005, Electronic Release, 7th ed., chap. 7 ("Foams"), Wiley-VCH, Weinheim 2005.

The envelope densities of the inventive polyurethane foams are preferably from 10 to 150 kg/m$^3$. Their envelope densities are particularly preferably from 20 to 50 kg/m$^3$.

The following starting components are used for the production of the isocyanate-based foams:

1. Aliphatic, cycloaliphatic, araliphatic, aromatic and heterocyclic polyisocyanates (e.g. W. Siefken in Justus Liebigs Annalen der Chemie, 562, pp. 75-136), preferably those of the formula $Q(NCO)_n$, in which n=from 2 to 4, preferably from 2 to 3, and Q is an aliphatic hydrocarbon radical having from 2 to 18, preferably from 6 to 10, carbon atoms, a cycloaliphatic hydrocarbon radical having from 4 to 15, preferably from 5 to 10, carbon atoms, an aromatic hydrocarbon radical having from 6 to 15, preferably from 6 to 13, carbon atoms, or an araliphatic hydrocarbon radical having from 8 to 15, preferably from 8 to 13, carbon atoms. Particular preference is generally given to the polyisocyanates which are readily accessible industrially and which derive from olylene 2,4- and/or 2,6-diisocyanate or from diphenylmethane 4,4'- and/or 2,4'-diisocyanate.

2. Compounds having at least two hydrogen atoms reactive towards isocyanates and whose molar mass is from 400 to 8000 g/mol ("polyol component"). These are not only compounds having amino groups, thio groups or carboxy groups, but also preferably compounds having hydroxy groups, in particular compounds having from 2 to 8 hydroxy groups. If the polyurethane foam is intended to be a flexible foam, it is preferable to use polyols whose molar masses are from 2000 to 8000 g/mol and which have from 2 to 6 hydroxy groups per molecule. If, in contrast, the intention is to produce a rigid foam, it is preferable to use highly branched polyols whose molar masses are from 400 to 1000 g/mol and which have from 2 to 8 hydroxy groups per molecule. The polyols are polyethers and polyesters and also polycarbonates and polyesteramides, as known per se for production of homogeneous and cellular polyurethanes and as described by way of example in German Offeniegungsschrift 28 32 253. According to the invention, preference is given to polyesters and polyethers having at least two hydroxy groups.

The inventive polyurethane foams can therefore be produced in the form of rigid or flexible foams by selecting the starting materials appropriately in a manner easily found in the prior art.

Further starting components may be compounds having at least two hydrogen atoms reactive towards isocyanates and having a molecular weight of from 32 to 399 g/mol. Here again these are compounds having hydroxy groups and/or amino groups and/or thio groups and/or carboxy groups, preferably compounds having hydroxy groups and/or amino groups, where these compounds serve as chain extenders or crosslinking agents. These compounds generally have from 2 to 8, preferably from 2 to 4, hydrogen atoms reactive towards isocyanates. Examples here are likewise described in German Offenlegungsschrift 28 32 253.

3. As blowing agents, water and/or volatile substances, e.g. n-pentane, isopentane, cyclopentane, acetone, halogen-containing alkanes, such as trichloromethane, methylene chloride or chlorofluoroalkanes, $CO_2$, and other compounds.

4. Concomitant use is optionally made of auxiliaries and additives, such as catalysts of the type known per se, surfactant additives, such as emulsifiers and foam stabilizers, reaction retarders, e.g. acidic substances, such as hydrochloric acid or organic acyl halides, or else cell regulators of the type known per se, such as paraffins or fatty alcohols and dimethylpolysiloxanes, and also pigments or dyes and further flame retardants, or else stabilizers to protect from the effects of ageing and weather, core discolouration inhibitors, plasticizers and fungistatic and bacteriostatic substances, and also fillers, such as barium sulphate, kieselguhr, carbon black or whiting (German Offenlegungsschrift 27 32 292). Particular core discolouration inhibitors that can be present are sterically hindered trialkylphenols, alkyl esters of 3-(3,5-di-tert-butyl-4-hydroxyphenyl)propionic acid, benzofuran-2-ones, secondary aromatic amines, phosphites, phenothiazines or tocopherols.

Other flame retardants that can be present alongside the oligomer mixtures according to the invention in the polyurethanes according to the invention are
a) organophosphorus compounds, such as triethyl phosphate, triphenyl phosphate, diphenyl cresyl phosphate, tricresyl phosphate, isopropylated or butylated aryl phosphates, aromatic bisphosphates, neopentyl glycol bis(diphenyl phosphate), chlorine-containing phosphoric esters, e.g. tris(chloroisopropyl) phosphate or tris(dichloropropyl) phosphate, dimethyl methanephosphonate, diethyl ethanephosphonate, dimethyl propanephosphonate, diethylphosphinic acid derivatives and diethylphosphinic salts, other oligomeric phosphates or phosphonates, hydroxylated phosphorus compounds, 5,5-dimethyl-1,3,2-dioxaphosphorinane 2-oxide derivatives, 9,10-dihydro-9-exa-10-phosphaphenanthrene 10-oxide (DOPO) and its derivatives,
b) inorganic phosphorus compounds, such as ammonium phosphate, ammonium polyphosphate, melamine phosphate, melamine polyphosphate,
c) nitrogen compounds, such as melamine, melamine cyanurate,
d) bromine compounds, such as alkyl esters of a tetrabromobenzoic acid, bromine-containing diols produced from tetrabromophthalic anhydride, bromine-containing polyols, bromine-containing diphenyl ethers,
e) inorganic flame retardants, such as aluminium hydroxide, boehrnite, magnesium hydroxide, expandable graphite and clay minerals.

Pages 104 to 123 of Kunststoff-Handbuch [Plastics handbook], Volume VII, Carl-Hanser-Verlag, Munich, 1993, describe other examples of the following materials that can optionally be used concomitantly according to the invention: surfactant additives and foam stabilizers, and also cell regulators, reaction retarders, stabilizers, flame-retardant substances, plasticizers, colourants and fillers, and also fungistatic and bacteriostatic substances, and also describe details of the mode of use and mode of action of the said additives.

The present invention further provides a process for producing flame-retardant polyurethanes via reaction of organic polyisocyanates with compounds having at least two hydrogen atoms reactive towards isocyanates and conventional blowing agents, stabilizers, catalysts, activators and/or other conventional auxiliaries and additives in the presence of at least one oligomer mixture according to the invention. The amount generally used here of the oligomer mixture according to the invention is from 0.5 to 30 parts by weight, preferably from 3 to 25 parts by weight, based in each case on 100 parts by weight of polyol component. The process is preferably carried out at a temperature of from 20 to 80'C.

The process for producing the polyurethanes according to the invention is carried out by reacting the reaction components described above in the single-stage process known per se, the prepolymer process or the semiprepolymer process, and machinery is often used here, for example that described in U.S. Pat. No. 2,764,565. Details of processing equipment which can also be used according to the invention are described on pages 139 to 192 of Kunsistoff-Handbuch Band VII, Polyurethane [Plastics handbook, Volume VII, Polyurethanes], edited by G. Oertel, Carl-Hanser-Verlag, Munich, Vienna, 1993.

The process according to the invention can also be used to produce cold-curing foams (GB Patent Specification 11 62 517, German Offenlegungsschrift 21 53 086). However, it is also of course possible to produce foams via slabstock foaming or by the double-conveyor-belt process known per se. Polyisocyanurate foams are produced in accordance with the processes and conditions known for this purpose.

The process according to the invention allows the production of flame-retardant polyurethane foams in the form of rigid or flexible foams by a continuous or batchwise production route or in the form of foamed mouldings. Preference is given to the process according to the invention in the production of flexible foams, where these are produced by a slabstock-foaming process.

The polyurethanes according to the invention, obtainable by the process according to the invention, are preferably used in furniture cushioning, in textile inlays, in mattresses, in vehicle seats, in armrests, in components, in seat cladding and dashboard cladding, in cable sheathing, in gaskets, in coatings, in lacquers, in adhesion promoters, and in adhesives and fibres.

The oligomer mixtures according to the invention, present in the polyurethanes according to the invention, or used in the process according to the invention, can be produced by the process described above, by analogy with known methods. A particular advantage here is that suitable selection of the synthetic conditions allows oligomer mixtures according to the invention which have a particular composition to be obtained as direct products of a process. Starting materials used here are available on an industrial scale and permit simple production of the desired final products.

The liquid oligomer mixtures according to the invention are easy to meter. They do not react with the other starting materials used for producing the polyurethane foams, and are therefore very easy to process as additives. Surprisingly, they can be processed either with polyether polyols or with polyester polyols. The foams produced with the oligomer mixtures according to the invention do not only comply with the requirements for flame retardancy but also exhibit particularly low fogging values.

The examples below provide further explanation of the invention, but there is no intention of any resultant restriction of the invention.

EXAMPLES

General Synthesis Specification for the Oligomer Mixtures (Synthesis Examples S1 to S5)

The amount (parts by weight) of phosphorus oxychloride stated in Table 1 was charged to a reactor with stirrer, dropping funnel, reflux condenser and vacuum equipment. The temperature of the phosphorus oxychloride was controlled to from 10 to 20° C. The amount of diethylene glycol stated in Table 1 was added dropwise under a vacuum of from 500 to 700 mbar. Once the dropwise addition had ended, the pressure was further lowered to a final value of from 5 to 15 mbar, and the temperature was raised to from 20 to 30° C. This gave an almost colourless, liquid residue.

The amount of ethanol stated in Table 1 was used as initial charge at from 20 to 30° C. in another reactor with stirrer, dropping funnel and reflux condenser, and the residue obtained above was admixed. Stirring of the mixture was continued at from 20 to 30° C. until the reaction was complete, and the mixture was then neutralized via addition of concentrated sodium hydroxide solution. A sufficient amount of dichloromethane and water was then added to give two clear liquid phases. These were separated, and distillation was used to free the organic phase from the dichloromethane, excess ethanol and water. This gave a residue of the oligomer mixtures according to the invention in the form of colourless liquids. The viscosities of the resultant products were determined at 23° C. with a commercially available falling-sphere viscometer, and are listed in Table 1.

Determination of the Average Number of the Repeating Units n̄ of the Molecules Corresponding to the Formula I in the Oligomer Mixture Analysis by gel permeation chromatography (GPC) showed that the resultant products were oligomer mixtures. The number-average molar masses $M_n$ of the oligomer mixtures were determined by GPC with tetrahydrofuran as eluent against polystyrene standards by a method based on DIN 55672-1:2007-08. The average number of the repeating units n̄ of the poly(alkylene phosphates) corresponding to the formula (I) present in an oligomer mixture was calculated by the following formula from the number-average molar mass $M_n$ measured:

$$\bar{n} = (M_n - M_E)/M_R$$

where n̄: average number of repeating units of the poly(alkylene phosphates) of the formula (I) present in the oligomer mixture, $M_n$: number-average molar mass in g/mol determined by gel permeation chromatography, $M_E$: sum of the molar masses of the end groups in g/mol and $M_R$: molar mass of the repeating unit in g/mol.

For the oligomer mixtures of poly(alkylene phosphates) of the formula (I) where $R^1 = R^2 = R^3 = R^4 =$ ethyl and $A = -CH_2CH_2OCH_2CH_2-$, $M_E = 182.16$ g/mol and $M_R = 194.14$ g/mol. Table 1 lists the results.

TABLE 1

Raw materials and parts by weight used for producing oligomer mixtures of poly(alkylene phosphates) of the formula (I) where $R^1 = R^2 = R^3 = R^4 =$ ethyl and $A = -CH_2CH_2OCH_2CH_2-$ for Synthesis Examples S1 to S5 and properties

| | Example | | | | |
|---|---|---|---|---|---|
| | S1 | S2 | S3 | S4 | S5 |
| Diethylene glycol | 235.3 | 428.2 | 466.4 | 118.7 | 118.7 |
| Phosphorus oxychloride | 476.9 | 736.0 | 1214 | 306.7 | 269.9 |
| Ethanol | 1225 | 2230 | 2428 | 618.2 | 618.2 |
| Viscosity [mPas] | 190 | 1423 | 40 | 58 | 85 |
| $M_n$ | 592 | 655 | 429 | 462 | 495 |
| n̄ | 2.11 | 2.44 | 1.27 | 1.44 | 1.61 |
| According to the invention | no | no | yes | yes | yes |

Production of Flexible Polyurethane Foams

TABLE 2

Raw materials used for producing flexible polyether foams for the compositions of Inventive Examples IE2, IE2 and IE3, and also of the Non-inventive Comparative Examples CE1 to CE6 (according to Table 4)

| Component | Function | Description |
|---|---|---|
| A | Polyol | Arcol ® 1105 (Bayer MaterialScience), polyether polyol with OH number 56 mg KOH/g |
| B | Blowing agent | Water |
| C | Catalyst | Addocat 108 ® (Rhein Chemie), 70% solution of bis(2-dimethylaminoethyl) ether in dipropylene glycol |
| D | Catalyst | Addocat ® SO (Rhein Chemie), tin(II) 2-ethylhexanoate |
| E | Stabilizer | Tegostab ® B 8232 (Degussa), silicone stabilizer |
| F1 | Flame retardant | Tris(2,3-dichloroisopropyl) phosphate, TDCP |
| F2 | Flame retardant | Diphenyl cresyl phosphate |
| F3 | Flame retardant | Diethylene glycol bis(diethyl phosphate) according to EP 1 746 129 A1 |
| F4 | Flame retardant | Fyrol ® PNX from ICL-IP (oligoineric phosphate ester of the formula I where $R^1 = R^2 = R^3 = R^4 =$ ethyl and A = ethylene, CAS Reg. No. 184538-58-7), $M_n$ = 640 g/mol from GCP (see above); formula (I) gives n̄ = 3.01; viscosity 1241 mPas at 23° C. |
| F5 | Flame retardant | Product from Synthesis Example S1, not according to the invention |
| F7 | Flame retardant | Product from Synthesis Example S3, according to the invention |
| F8 | Flame retardant | Product from Synthesis Example S4, according to the invention |
| F9 | Flame retardant | Product from Synthesis Example S5, according to the invention |
| G | Diisocyanate | Desmodur ® T 80 (Bayer MaterialScience), tolylene diisocyanate, isomer mixture |

Production of Flexible Polyether Foams

Table 2 states the raw materials for producing flexible polyether foams, Table 4 states the nature and amount of the components which, with the exception of the diisocyanate (component G), were mixed to give a homogeneous mixture. The diisocyanate was then added and incorporated by brief vigorous stirring. The envelope density of the flexible polyurethane foam obtained after a cream time of from 15 to 20 s and a full rise time of from 170 to 200 s was 33 kg/m³. All of the experiments gave uniformly fine-pored foams.

TABLE 3

Raw materials used for producing flexible polyester foams for the compositions of Inventive Examples IE4, IE5 and IE6, and also of the Non-inventive Comparative Examples CE7 to CE13 (according to Table 5)

| Component | Function | Description |
|---|---|---|
| A | Polyol | Desmophen ® 2200 B (Bayer MaterialScience), polyester polyol with OH number 60 mg KOH/g |
| B | Blowing agent | Water |
| C | Catalyst | Niax ® A-30(Momentive), amine |
| D | Catalyst | Addocat ® 117 (Rhein Chemie), tertiary amine |
| E | Stabilizer | Tegostab ® B 8324 (Degussa), silicone stabilizer |
| F1 | Flame retardant | Tris(2,3-dichlorolsopropyl) phosphate, TDCP, CAS Reg. No. 13674-87-8 |
| F2 | Flame retardant | Diphenyl cresyl phosphate, CAS Reg. No. 26444-49-5 |
| F3 | Flame retardant | Diethylene glycol bis(diethyl phosphate) according to EP 1 746 129 A1 |
| F4 | Flame retardant | Fyrol ® PNX from ICL-IP (oligotneric phosphate ester of the formula I where $R^1 = R^2 = R^3 = R^4$ = ethyl and A = ethylene, CAS Reg. No. 184538-58-7), $M_n$ = 640 g/mol from GCP (see above); formula (I) gives $\bar{n}$ = 3.01; viscosity 1241 mPas at 23° C. |
| F5 | Flame retardant | Product from Synthesis Example S1 |
| F6 | Flame retardant | Product from Synthesis Example S2 |
| F7 | Flame retardant | Product from Synthesis Example S3, according to the invention |
| F8 | Flame retardant | Product from Synthesis Example S4, according to the invention |
| F9 | Flame retardant | Product from Synthesis Example S5, according to the invention |
| G | Diisocyanate | Desmodur ® T 80 (Bayer MaterialScience), tolylene diisocyanate, isomer mixture |
| H | Diisocyanate | Desmodur ® T 65 (Bayer MaterialScience), tolylene diisocyanate, isomer mixture |

Production of Flexible Polyester Foams

Table 3 states the raw materials for producing flexible polyester foams. Table 5 states the nature and amount of the components which, with the exception of the two diisocyanates (components G and H), were mixed to give a homogeneous mixture. The two premixed diisocyanates were then added and incorporated by brief vigorous stirring. The envelope density of the flexible polyurethane foam obtained after a cream time of from 10 to 15 s and a full rise time of from 80 to 90 s was 29 kg/m³. The foam structure of the flexible polyester foams depended on the flame retardants used. It is recorded in Table 5 as "uniformly fine-pored" ("uf") or "non-uniformly coarse-pored" ("nc").

Test Results for Flexible Polyurethane Foams

Determination of Flame Retardancy

The flexible polyurethane foams were tested in accordance with the specifications of the Federal Motor Vehicle Safety Standards FMVSS 302 and allocated to fire classes SE (self-extinguishing), SE/NBR (self-extinguishing/no burning rate), SE/BR (self-extinguishing/with burning rate), BR (burning rate) and RB (rapid burning). The fire tests were carried out five times for each Example. The worst result from each series of five has been given in Table 4 and, respectively, Table 5.

Determination of Fogging

The fogging behaviour of the flexible polyurethane foams was studied in accordance with DIN 75201 B. Table 4 gives the amounts of condensate measured after storage at 100° C. for 16 h.

TABLE 4

Composition (parts by weight) and test results for Inventive Examples IE1 to IE3 and for Non-inventive Comparative Examples CE1 to CE6 relating to flexible polyether foams

| Example | CE1 | CE2 | CE3 | CE4 | CE5 | CE6 | IE1 | IE2 | IE3 |
|---|---|---|---|---|---|---|---|---|---|
| A | 100 | 100 | 100 | 100 | 100 | 100 | 100 | 100 | 100 |
| B | 3.0 | 3.0 | 3.0 | 3.0 | 3.0 | 3.0 | 3.0 | 3.0 | 3.0 |
| C | 0.08 | 0.08 | 0.08 | 0.08 | 0.08 | 0.08 | 0.08 | 0.08 | 0.08 |
| D | 0.16 | 0.16 | 0.16 | 0.16 | 0.16 | 0.16 | 0.16 | 0.16 | 0.16 |
| E | 0.80 | 0.80 | 0.80 | 0.80 | 0.80 | 0.80 | 0.80 | 0.80 | 0.80 |
| F1 | 6 | | | | | | | | |
| F2 | | 6 | | | | | | | |
| F3 | | | 6 | | | | | | |
| F4 | | | | 6 | | | | | |
| F5 | | | | | 6 | | | | |
| F7 | | | | | | | 6 | | |
| F8 | | | | | | | | 6 | |
| F9 | | | | | | | | | 6 |

TABLE 4-continued

Composition (parts by weight) and test results for Inventive Examples IE1 to IE3 and for Non-inventive Comparative Examples CE1 to CE6 relating to flexible polyether foams

| Example | CE1 | CE2 | CE3 | CE4 | CE5 | CE6 | IE1 | IE2 | IE3 |
|---|---|---|---|---|---|---|---|---|---|
| G | 40.9 | 40.9 | 40.9 | 40.9 | 40.9 | 40.9 | 40.9 | 40.9 | 40.9 |
| FMVSS class | RB | SE | BR | SE | SE | SE | SE | SE | SE |
| Fogging condensate [mg] in accordance with DIN 75201 B | 0.19 | 0.72 | 0.59 | 0.37 | 0.33 | 0.21 | 0.32 | 0.31 | 0.28 |

Evaluation of the Results Relating to Flexible Polyether Foams

In the absence of a flame retardant (Comparative Example CE1) the flexible polyurethane foam is rapidly consumed by burning (FMVSS fire class RB), but exhibits a very low fogging value. A foam with tris(dichloroisopropyl) phosphate (Comparative Example CE2) exhibits a substantial contribution of the flame retardant additive to fogging and achieves the best FMVSS fire class SE (self-extinguishing) in all repetitions of the fire test. However, tris(dichloroisopropyl) phosphate has the attendant disadvantages described above of a halogen-containing flame retardant. Although the use of the halogen-free flame retardant diphenyl cresyl phosphate (Comparative Example CE3) avoids this problem and also achieves a relatively low fogging value, the flame-retardant effect is inadequate, with FMVSS fire class BR. The flame retardants used in the Comparative Examples CE4 to CE6 have a very good flame-retardant effect (all self-extinguishing) and also give relatively low fogging values.

Inventive Examples IE1 to IE3 show that the flexible polyurethane foams according to the invention likewise achieve the best fire class SE (self-extinguishing) in all repetitions of the fire test and feature the lowest fogging values. In particular, fogging is lower in IE1 to IE3 than in Comparative Example CE4, in which the flame retardant diethylene glycol bis(diethyl phosphate) (F3) was processed. F3 is structurally related to the oligomer mixtures according to the invention, corresponding to formula II where $R^1=R^2=R^3=R^4=$ethyl and $A=-CH_2CH_2OCH_2CH_2-$ and $\bar{n}=1.00$.

TABLE 5

Composition (parts by weight) and test results for Inventive Examples IE4 to IE6 and for Non-inventive Comparative Examples CE7 to CE13 relating to flexible polyester foams

| Example | CE7 | CE8 | CE9 | CE10 | CE11 | CE12 | CE13 | IE4 | IE5 | IE6 |
|---|---|---|---|---|---|---|---|---|---|---|
| A | 100 | 100 | 100 | 100 | 100 | 100 | 100 | 100 | 100 | 100 |
| B | 4.0 | 4.0 | 4.0 | 4.0 | 4.0 | 4.0 | 4.0 | 4.0 | 4.0 | 4.0 |
| C | 0.25 | 0.25 | 0.25 | 0.25 | 0.25 | 0.25 | 0.25 | 0.25 | 0.25 | 0.25 |
| D | 0.25 | 0.25 | 0.25 | 0.25 | 0.25 | 0.25 | 0.25 | 0.25 | 0.25 | 0.25 |
| E | 1.0 | 1.0 | 1.0 | 1.0 | 1.0 | 1.0 | 1.0 | 1.0 | 1.0 | 1.0 |
| F1 | | 4 | | | | | | | | |
| F2 | | | 4 | | | | | | | |
| F3 | | | | 4 | | | | | | |
| F4 | | | | | 4 | | | | | |
| F5 | | | | | | 4 | | | | |
| F6 | | | | | | | 4 | | | |
| F7 | | | | | | | | 4 | | |
| F8 | | | | | | | | | 4 | |
| F9 | | | | | | | | | | 4 |
| G | 24.1 | 24.1 | 24.1 | 24.1 | 24.1 | 24.1 | 24.1 | 24.1 | 24.1 | 24.1 |
| H | 24.1 | 24.1 | 24.1 | 24.1 | 24.1 | 24.1 | 24.1 | 24.1 | 24.1 | 24.1 |
| Foam structure | uf | uf | uf | uf | nc | nc | nc | uf | uf | uf |
| FMVSS class | RB | SE | BR | SE | — | — | — | SE | SE | SE |

Evaluation of the Results Related to Flexible Polyester Foams

In the absence of a flame retardant (Comparative Example CE7) the flexible polyurethane foam is rapidly consumed by combustion (FMVSS fire class RB). A foam with tris(dichloroisopropyl) phosphate (Comparative Example CE8) achieves the best FMVSS fire class SE (self-extinguishing) in all repetitions of the fire test. However, tris(dichloroisopropyl) phosphate has the attendant disadvantages described above of a halogen-containing flame retardant. Although the use of the halogen-free flame retardant diphenyl cresyl phosphate (Comparative Example CE9) avoids this problem, the flame-retardant effect is inadequate, with FMVSS fire class BR. The Comparative Example CE10 likewise achieves the best classification in the fire test. The flame retardants F4 ($\bar{n}=3.01$), F5 ($\bar{n}=2.11$) and F6 ($\bar{n}=2.44$) (Comparative Examples CE11 to CE13) proved to be incompatible with the polyester polyols. These incompatibilities were apparent in a non-uniform, coarse-pored structure of the flexible polyester foams. Foams of this type cannot be used for the typical applications of flexible foam. For this reason, no FMVSS classes were determined for the Comparative Examples CE11 to CE13.

Inventive Examples IE4 to IE6 show that the oligomer mixtures according to the invention can also be processed with polyester polyols without difficulty to give flexible polyurethane foams, and that these likewise achieve the best fire class SE (self-extinguishing) in all repetitions of the fire test.

If the results from flexible polyether foams and flexible polyester foams are compared, it is apparent that the oligomer mixtures according to the invention can be used to produce not only flexible polyether foams but also flexible polyester foams, and that these also exhibit very good flame retardancy and low fogging values. None of the comparative products exhibits this combination of properties.

What is claimed is:

1. An oligomer mixture consisting essentially of at least three different poly(alkylene phosphates) of the formula (I),

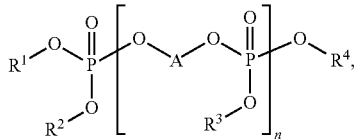
(I)

in which
R$^1$, R$^2$, R$^3$ and R$^4$ mutually independently are a straight-chain or branched C$_1$-C$_8$-alkyl moiety or a straight-chain or branched C$_1$-C$_4$-alkoxyethyl moiety,
A is a straight-chain, branched and/or cyclic C$_4$-C$_{20}$-alkylene moiety, or
a moiety of the formula —CH$_2$—CH═CH—CH$_2$—,
a moiety of the formula —CH$_2$—C≡C—CH$_2$—,
a moiety of the formula —CHR$^5$—CHR$^6$—(O—CHR$^7$—CHR$^8$)$_a$—, in which R$^5$, R$^6$, R$^7$ and R$^8$ are mutually independently methyl or H, wherein at least one of R$^5$, R$^6$, R$^7$ and R$^8$ is H,
a moiety of the formula —CHR$^5$—CHR$^6$—S(O)$_b$—CHR$^7$—CHR$^8$—, or a moiety of the formula —(CHR$^5$—CHR$^6$—O)$_c$—R$^9$—(O—CHR$^7$—CHR$^8$)$_d$—, in which R$^5$, R$^6$, R$^7$ and R$^8$ are mutually independently H or mehtyl,
and
a is an integer from 1 to 5,
b is an integer from 0 to 2,
c and d are mutually independently an integer from 1 to 5,
and
R$^9$ is a moiety of the formula —CH$_2$—CH═CH—CH$_2$—, a moiety of the formula —CH$_2$—C≡C—CH$_2$—, a 1,2-phenylene moiety, a 1,3-phenylene moiety, a 1,4-phenylene moiety, a moiety of the formula (II)

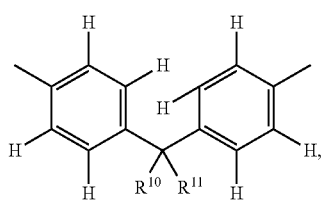
(II)

a moiety of the formula (III)

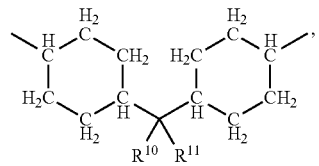
(III)

a moiety of the formula (IV)

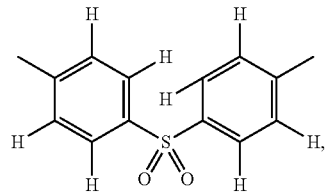
(IV)

a moiety of the formula —C(═O)—R$^{12}$—C(═O)—,
where
R$^{10}$ and R$^{11}$ are mutually independently respectively H or C$_1$-C$_4$-alkyl or R$^{10}$ and R$^{11}$ together are an optionally alkyl-substituted ring having from 4 to 8 carbon atoms, and
R$^{12}$ is a straight-chain, branched and/or cyclic C$_2$-C$_8$-alkylene moiety, a 1,2-phenylene moiety, a 1,3-phenylene moiety, or a 1,4-phenylene moiety, and
n is an integer from 0 to 100,
with the proviso that the at least three poly(alkylene phosphates) of the formula (I) differ from one another at least in the number n of the repeating units, and an average number of the repeating units $\bar{n}$ of the at least three poly(alkylene phosphates) of the formula (I) is greater than 1.10 and smaller than 2.00.

2. The oligomer mixture according to claim 1, wherein:
R$^1$, R$^2$, R$^3$ and R$^4$ are identical and are ethyl, n-propyl, isopropyl, n-butyl, isobutyl or n-butoxyethyl,
A is a straight-chain C$_4$-C$_6$-alkylene moiety, or a moiety of the formulae

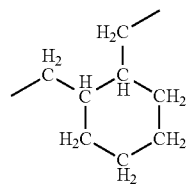
(V)

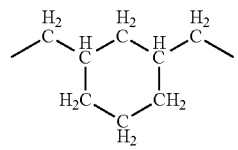
(VI)

or

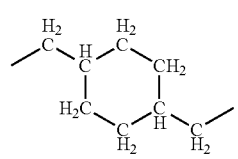
(VII)

or a moiety —CHR$^5$—CHR$^6$—(O—CHR$^7$—CHR$^8$)$_a$—, in which a is an integer from 1 to 2 and R$^5$, R$^6$, R$^7$ and R$^8$ are identical and are H,
or a moiety —(CHR$^5$—CHR$^6$—O)$_c$—R$^9$—(O—CHR$^7$—CHR$^8$)$_d$—, in which c and d are mutually independently an integer from 1 to 2, $R^5$, $R^6$, $R^7$ and $R^8$ are identical and are H, and $R^9$ is a moiety of the formula (II), where $R^{10}$ and $R^{11}$ are identical and are methyl, and n is an integer from 0 to 20.

3. The oligomer mixture according to claim 1, wherein the average number of the repeating units $\bar{n}$ is greater than 1.20 and smaller than 1.90.

4. The oligomer mixture according to claim 1, wherein the oligomer mixture is halogen-free.

5. The oligomer mixture according to claim 1, wherein the oligomer mixture has a dynamic viscosity of 20 to 1000 mPas at 23° C.

6. A process for producing an oligomer mixture according to claim 1, the process comprising:
  reacting in a first stage, a dihydroxy compound of the formula HO-A-OH, in which A is defined as in claim 1, with phosphorus oxychloride $POCl_3$, where the amount used of dihydroxy compound of the formula HO-A-OH per mole of phosphorus oxychloride is more than 1.0 mol and less than 2.0 mol to produce a resultant mixture of oligomeric chlorophosphates of the formula (VIII)

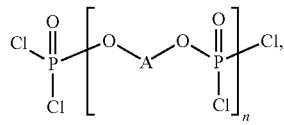

(VIII)

in which n is an integer from 0 to 100; and
reacting in a second stage, the mixture of oligomeric chlorophosphates with at least one monohydroxy compound of the formula

M-OH     (IX), in which M is $R^1$, $R^2$, $R^3$ or $R^4$, and
the definitions of $R^1$, $R^2$, $R^3$ and $R^4$ are those stated in claim 1.

7. Flame retardant preparations comprising at least one oligomer mixture according to claim 1, one or more flame retardants B) differing from the oligomer mixture, and optionally one or more auxiliaries C).

8. The flame retardant preparation according to claim 7, wherein the flame retardant B) is selected from the group consisting of triethyl phosphate, triphenyl phosphate, diphenyl cresyl phosphate, tricresyl phosphate, isopropylated or butylated aryl phosphates, bisphenol A bis(diphenyl phosphate), resorcinol bis(diphenyl phosphate), neopentyl glycol bis(diphenyl phosphate), tris(chloroisopropyl) phosphate, tris(dichloropropyl) phosphate, dimethyl methanephosphonate, diethyl ethanephosphonate, dimethyl propanephosphonate, diethyl phosphinic acid derivatives and diethyl phosphinic acid salts, oligomeric phosphates or phosphonates, hydroxylated phosphorus compounds, 5,5-dimethyl-1,3,2-dioxaphosphorinane 2-oxide derivatives, 9,10-dihydro-9-oxa-10-phosphaphenanthrene 10-oxide (DOPO) and its derivatives, ammonium phosphate, ammonium polyphosphate, melamine phosphate, melamine polyphosphate, melamine, melamine cyanurate, alkyl ester of a tetrabromobenzoic acid, bromine-containing diols produced from tetrabromophthalic anhydride, bromine-containing polyols, bromine-containing diphenyl ethers, aluminium hydroxide, boehmite, magnesium hydroxide, expandable graphite and clay minerals.

9. Flams-retardant polyurethanes comprising at least one oligomer mixture according to claim 1.

10. The flame-retardant polyurethanes according to claim 9, wherein the flame-retardent polyurethanes comprise polyurethane foams.

11. A process for producing flame-retardant polyurethanes according to claim 9, the process comprising reacting at least one organic polyisocyanate with at least one compound which has at least two hydrogen atoms reactive towards isocyanates in the presence of at least one oligomer mixture according to claim 1.

12. The process according to claim 11, further comprising using 3 to 25 parts by weight of oligomer mixture for every 100 parts by weight of compound having at least two hydrogen atoms reactive towards isocyanates.

13. The process according to claim 11, wherein the compound having at least two hydrogen atoms reactive towards isocyanates comprises a polyether polyol.

14. The process according to claim 11, wherein the compound having at least two hydrogen atoms reactive towards isocyanates comprises a polyester polyol.

15. Mouldings, lacquers, adhesives, coatings, adhesion promoters and fibres comprising polyurethanes according to claim 9.

16. An oligomer mixture comprising poly(alkylene phosphates), wherein the poly(alkylene phosphates) in the mixture consist of at least three different poly(alkylene phosphates) of the formula (I)

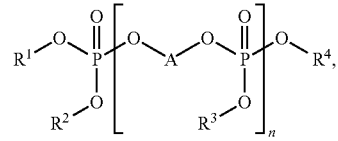

(I)

in which
  $R^1$, $R^2$, $R^3$ and $R^4$ mutually independently are a straight-chain or branched $C_1$-$C_8$-alkyl moiety or a straight-chain or branched $C_1$-$C_4$-alkoxyethyl moiety,
  A is a straight-chain, branched and/or cyclic $C_4$-$C_{20}$-alkylene moiety, or a moiety of the formula —$CH_2$—CH=CH—$CH_2$—, a moiety of the formula —$CH_2$—C≡C—$CH_2$—, a moiety of the formula —$CHR^5$—$CHR^6$—(O—$CHR^7$—$CHR^8$)$_a$—, a moiety of the formula —$CHR^5$—$CHR^6$—S(O)$_b$—$CHR^7$—$CHR^8$—, or a moiety of the formula —($CHR^5$—$CHR^6$—O)$_c$—$R^9$—(O—$CHR^7$—$CHR^8$)$_d$—,
  in which
    a is an integer from 1 to 5,
    b is an integer from 0 to 2,
    c and d are mutually independently an integer from 1 to 5,
    $R^5$, $R^6$, $R^7$ and $R^8$ are mutually independently H, and
    $R^9$ is a moiety of the formula —$CH_2$—CH=CH—$CH_2$—, a moiety of the formula —$CH_2$—C≡C—$CH_2$—, a 1,2-phenylene moiety, a 1,3-phenylene moiety, a 1,4-phenylene moiety, a moiety of the formula (II)

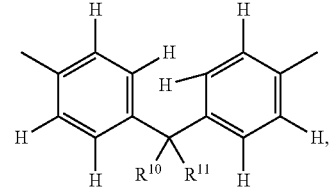

(II)

a moiety of the formula (III)

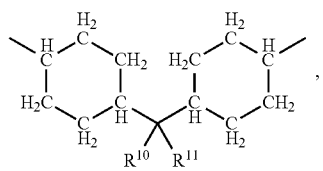
(III)

a moiety of the formula (IV)

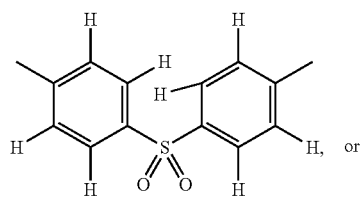
(IV)

a moiety of the formula —C(=O)—R$^{12}$—C(=O)—, where

R$^{10}$ and R$^{11}$ are mutually independently respectively H or C$_1$-C$_4$-alkyl or R$^{10}$ and R$^{11}$ together are an optionally alkyl-substituted ring having from 4 to 8 carbon atoms, and R$^{12}$ is a straight-chain, branched and/or cyclic C$_2$-C$_8$-alkylene moiety, a 1,2-phenylene moiety, a 1,3-phenylene moiety, or a 1,4-phenylene moiety, and n is an integer from 0 to 100, with the proviso that the at least three poly(alkylene phosphates) of the formula (I) differ from one another at least in the number n of the repeating units, and an average number of the repeating units $\overline{n}$ of the at least three poly(alkylene phosphates) of the formula (I) is greater than 1.10 and smaller than 2.00.

17. The oligomer mixture according to claim 16, wherein the oligomer mixture consists of at least three different poly(alkylene phosphates) of the formula (I).

18. The oligomer mixture according to claim 1, wherein A is a moiety

—CHR$^5$—CHR$^6$—(O—CHR$^7$—CHR$^8$)$_a$—, in which a is an integer from 1 to 2 and R$^5$, R$^6$, R$^7$ and R$^8$ are identical and are H.

* * * * *